United States Patent [19]

Lambert et al.

[11] Patent Number: 4,511,658
[45] Date of Patent: Apr. 16, 1985

[54] COLORIMETRIC DETECTOR FOR FORMALDEHYDE VAPOR

[75] Inventors: Jack L. Lambert, Manhattan; Yuan C. Chiang, Salina, both of Kans.

[73] Assignee: Kansas State University Research Foundation, Manhattan, Kans.

[21] Appl. No.: 470,510

[22] Filed: Feb. 28, 1983

[51] Int. Cl.³ ............................................. G01N 21/78
[52] U.S. Cl. ..................................... 436/130; 422/56; 422/57; 427/162; 436/166; 548/263
[58] Field of Search ................ 427/162; 436/164, 166, 436/169, 128, 130; 422/36, 55; 548/263

[56] References Cited

U.S. PATENT DOCUMENTS

| | | | |
|---|---|---|---|
| 3,645,696 | 2/1972 | Iannacone et al. | 436/166 |
| 4,438,206 | 3/1984 | Nakajima et al. | 436/130 |
| 4,471,055 | 9/1984 | Opp | 436/128 |

OTHER PUBLICATIONS

Dickinso et al., "A New Sensitive and Specific Test for the Detection of Aldehydes: Formation of 6-Mercapto-3-Substituted-5-Triazalo[4,3,-b]-5-Tetrazines", *Chemical Communications*, 1719–1720 (1970).
Kurzer et al., "Chemistry of Biureas–I", *Tetrahedron*, 33 (15), 1999–2006 (1977).

*Primary Examiner*—Arnold Turk
*Assistant Examiner*—John Donofrio

[57] ABSTRACT

A sensitive colorimetric detector for formaldehyde vapor is prepared by applying a ketone solution of 4-amino-3-hydrazino-5-mercapto-1,2,4-triazole (AHMT) to a support coated with a stable metal bicarbonate to form a compound from which the ketone can be displaced by formaldehyde to yield a chromogen developing a purple color proportional to the amount of formaldehyde. The detector is sensitive to gaseous formaldehyde in air at concentrations below 2 ppm.

8 Claims, No Drawings

COLORIMETRIC DETECTOR FOR FORMALDEHYDE VAPOR

GRANT REFERENCES

This invention was developed in part under National Science Foundation Grant CHE-7915217, and under National Science Foundation Grant SPI-8013291.

BACKGROUND AND PRIOR ART

The field of this invention is the detection of minute concentrations of formaldehyde vapor in gases, particularly the detection of formaldehyde concentrations in air in the ppm and sub-ppm range. The kind of detection involved is a colorimetric reaction producing a chromogen the color intensity of which is proportional to the amount of formaldehyde vapor to which the detector is exposed. Such detectors can be qualitative, semi-quantitative, or quantitative, and can be read with standard reflectance spectrophotometers, or visually by the eye using color comparison standards. The invention here relates to the novel chemistry of the detector, and its method of preparation and use.

No directly relevant prior art is known. Prior methods for detecting low concentrations of formaldehyde in air have followed entirely different principles and used entirely different chemistry. However, the primary reagent used to prepare the detector of this invention is a known colorimetric reagent. This reagent is 4-amino-3-hydrazino-5-mercapto-1,2,4-triazole (AHMT). This compound is available commercially under the trademark name "Purpald" from Aldrich Chemical Co., Milwaukee, Wis. Heretofore, it has been used primarily to determine aldehydes by colorimetric reaction in alkaline aqueous solution. See *Chromatographia*, 5, 307308 (1972) and *Chemical Communications*, 1970, 1719–1720. AHMT combines with phase-transfer catalysts so as to provide an aldehyde classification test. *J. Chem. Educ.*, 55, 206 (1978). It has also been shown that the compound AHMT is the triazole formed as the common product in the hydrazinolysis of many thioureido compounds. *Anal. Chem.*, 41, 1324–1327 (1969).

SUMMARY OF INVENTION

This invention is based on the discovery that a highly sensitive colorimetric detector for formaldehyde vapor can be prepared from three chemical reagents: 4-amino-3-hydrazino-5-mercapto-1,2,4-triazole (AHMT), a volatile liquid ketone such as acetone or methylethyl ketone, and a stable metal bicarbonate such as sodium or potassium bicarbonate. A coating of the metal bicarbonate is formed on an inert solid support, such as by applying an aqueous solution of the bicarbonate, and drying the applied solution to form a solid phase layer of the metal bicarbonate. AHMT is then applied to the bicarbonate layer in a solution of a volatile liquid ketone. The ketone forms a compound with the AHMT from which the ketone can be displaced by formaldehyde. The AHMT-ketone aminal compound thus produced is believed to be in anionic form on the bicarbonate. However, the exact structure of the compound formed has not been determined with certainty. Other salts, such as the carbonate and iodate salts of sodium and potassium, were investigated as supports but they were not as satisfactory as the bicarbonate salts.

After the application of the ketone solution of the AHMT, the unreacted ketone is evaporated leaving the formaldehyde-reactive compound in solid phase. This completes the preparation of the formaldehyde detector. When properly used, it has been found to be sensitive to formaldehyde vapor below 2 ppm in air down to sub-ppm concentrations.

With detectors freshly prepared as described, the color-forming reaction with formaldehyde occurs readily when there is sufficient moisture present in the chromogen-providing layer. When the detector layer is substantially free of moisture, the formaldehyde reacts but that the oxidation reaction needed to produce the purple color requires the presence of a small amount of water. It is preferable to expose the dry reagent papers to the sample air containing formaldehyde. A reaction will then occur in which the formaldehyde displaces the ketone. After moistening the formaldehyde-containing compound with a mixture of acetone containing a limited amount of water, it reacts with atmospheric oxygen to produce the compound having the purple color. The moistening of the detector layer is preferably carried out quickly to minimize the dissolving of any substantial amount of either the AHMT-ketone-aminal reagent or the metal bicarbonate. It has been found that this can be accomplished by using a mixture of water and ketone containing a limited amount of water. The water in the single phase mixture reduces the solubility of the AHMT compound, and the ketone reduces the solubility of the metal bicarbonate.

DETAILED DESCRIPTION

The primary reagent for preparing the colorimetric detector of this invention is 4-amino-3-hydrazino-mercapto-1,2,4-triazole, referred to herein as "AHMT". This compound is available commercially, being sold, for example, under the trademark "Purpald" by Aldrich Chemical Co., Milwaukee, Wis. The other reagents may be selected as follows.

Any metal bicarbonate may be used which is water-soluble and stable both in aqueous solution and in solid phase. The akali metal bicarbonates, particularly sodium and potassium bicarbonate, are preferred.

The volatile liquid ketone is preferably acetone or methylethyl ketone. However, in accordance with the discovery underlying the present invention, other volatile liquid ketones can be employed providing they form compounds with AHMT from which the ketone can be displaced by formaldehyde.

A wide variety of inert solid supports can be employed for the detector layer. The supports may be in the form of sheets, strips, or granules. For example, filter papers formed from cellulose fibers or glass fibers can be used, as well as woven cloth formed from cotton or synthetic fibers. Granular absorbents which may be used include silica gel, alumina, and zeolites. Preferably, the support should be readily wettable by aqueous ketone solutions.

As a first step in preparing the detectors, the support is provided with a surface and/or impregnated coating of solid phase metal bicarbonate. In one procedure, the metal bicarbonate is dissolved in water, and the support is soaked in the solution. The aqueous solution does not need to be saturated with the bicarbonate. In fact, the concentration is merely a matter of convenience. For example, concentrations of from 2 to 8% by weight of the metal carbonate in water can be used. After the application of the aqueous solution, the support is dried with evaporation of water to produce the solid phase layer of the bicarbonate. With porous supports, the layer may extend through the support and be formed on both sides or surfaces. When porous granules are used as a support, they will be impregnated with the bicarbonate as well as having the bicarbonate on the outer surfaces of the granules. It is desirable to have a large excess bicarbonate present over that to be reacted with the AHMT compound.

In the next step, the AHMT is applied in ketone solution to the metal bicarbonate. The use of a saturated solution is desirable since the AHMT has limited solubility in ketones such as acetone and methylethyl ketone. However, lower concentrations than the saturation concentration can be used. The ketone solution of AHMT is applied to the bicarbonate layer on the support. A small amount of the ketone reacts with the AHMT to form a compound from which the ketone can be displaced by formaldehyde. The remaining ketone, which comprises most of the applied ketone, is removed by evaporation, leaving the AHMT-ketone compound in solid phase on the solid phase layer of bicarbonate. A small amount of the bicarbonate is also believed to react with the deposited AHMT-ketone compound to convert the sulfhydryl group of the compound to anionic salt form.

Although not known with certainty, the key chemical reactions are believed to be represented by the following equations wherein the representative reactants shown are AHMT, acetone, and sodium bicarbonate.

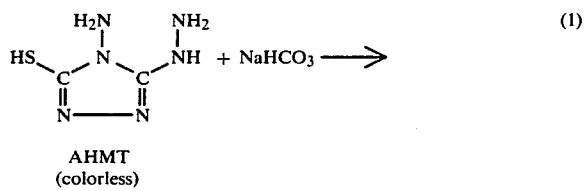

AHMT
(colorless)

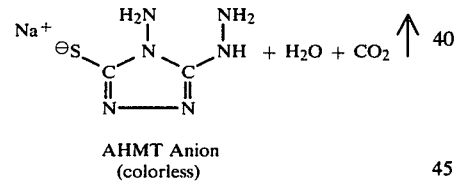

AHMT Anion
(colorless)

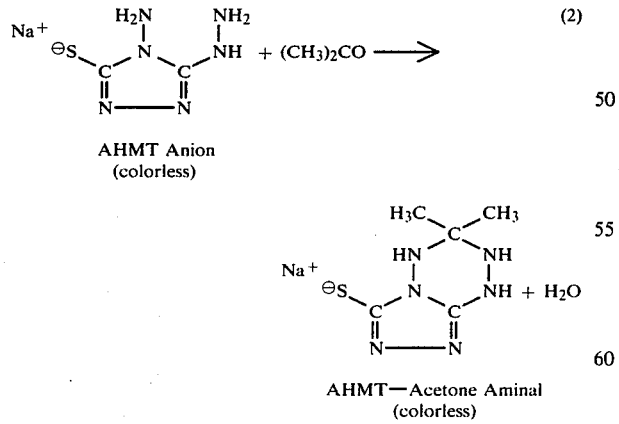

AHMT—Acetone Aminal
(colorless)

The detectors may be used immediately as prepared with the detector coating contains some moisture. This may be residual moisture from the aqueous bicarbonate solution, or it may be atmospheric moisture condensed by the cooling of the layer during the evaporation of the ketone. It will usually be desirable, however, to prepare and store the detectors for several days or weeks prior to use. For this purpose, the detector layers may be dried to a substantially anhydrous condition. In dry, nearly anhydrous, condition, the detectors are stable in storage.

The prepared detector is used by exposing it to air or a sample of air believed to contain minute amounts of formaldehyde. As will be subsequently further illustrated, concentrations of formaldehyde can be detected in the range from 0.2 to 2 ppm. Although the color-forming reaction is not known with certainty, it is believed to be represented by the following equations.

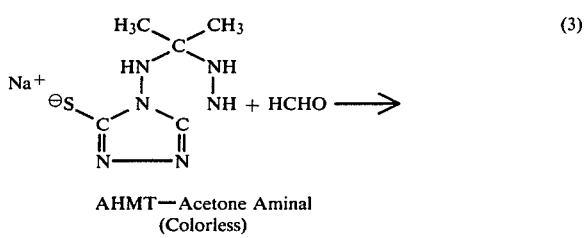

AHMT—Acetone Aminal
(Colorless)

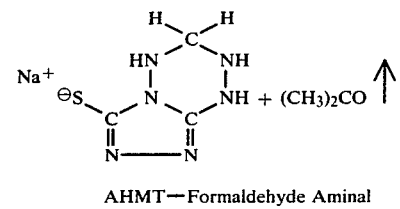

AHMT—Formaldehyde Aminal
(Colorless)

A special remoistening procedure supplies water to enable atmospheric oxygen to produce color in the exposed detector layer without any substantial dissolving of its components. The rewetting can be carried out with a mixture of ketone and water, such as acetone and water or methylethyl ketone and water. The water content of the mixture is limited to the range of about 5 to 20% water by volume, and preferably to about 7 to 15% water. Sufficient water is then present for the color-forming reaction while the detector layer and its reacting compound remains substantially in solid phase.

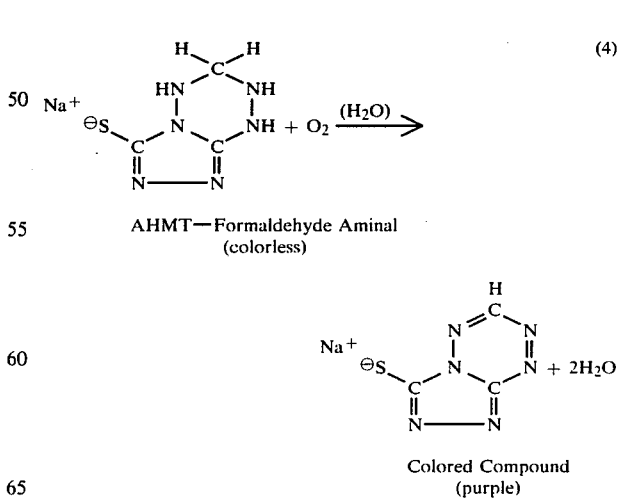

The detector compound as shown in Equation (3) above has been formed from acetone and sodium bicarbonate. This compound reacts with the formaldehyde in the air so that the formaldehyde displaces the acetone, resulting in an AHMT-formaldehyde aminal compound, which in the presence of moisture reacts with the oxygen in the air, according to Equation (4) to produce the chromogen having a purple color. It has been found that the color-forming reactions, as represented by Equations (3) and (4) are highly selective to formaldehyde. Other aldehydes, such as acetaldehyde, propionaldehyde, and benzaldehyde, do not produce the color reaction when present as a gas in air.

The reactions for preparing the aminal reagent and the reactions occuring during their use can all be carried out at ordinary ambient temperatures, such at temperatures from about 20° to 30° C. In the drying steps to remove the water in the application of bicarbonate salt to the detector support, it is adviseable to use moderate drying temperatures, such as temperatures ranging from 50° to 70° C. with large volume air flow to facilitate drying.

The technical basis of the present invention can be more fully understood from the following experimental examples.

EXPERIMENTAL EXAMPLES

All compounds were analytical grade or the purest grade available. Solutions were prepared with deionized water or A.C.S. certified-grade acetone, as appropriate. Reflectance measurements were made with a Coleman Model 124 spectrophotometer (Perkin-Elmer Corp.) modified for reflectance measurements. See Lambert et al, *Anal. Chem.*, 54, 1227 (1982).

Reagent papers. Filter paper circles, 4.2-cm diameter (Whatman #1 grade), were soaked in 8% aqueous sodium bicarbonate solution for two minutes, the excess solution drained, and the papers dried in an oven at approximately 70° C. on a glass plate. The dried papers were then soaked in a saturated acetone solution of 4-amino-3-hydrazino-5-mercapto-1,2,4-triazole (AHMT) and air-dried at room temperature. The prepared reagent papers are stable when stored in a sealed container.

Formaldehyde generator. A device for the production of small concentrations of formaldehyde from paraformaldehyde at room temperature was employed. The weight loss of paraformaldehyde (the amount of formaldehyde generated) was determined at the time of each set of analyses comprising the calibration curves, the reagent papers being exposed to the determined concentrations of formaldehyde.

Developing solution. A 90% acetone-10% water solution provides the small amount of moisture required for the air oxidation of the exposed reagent to the purple chromagen without dissolution of the reagent. Full color development occurs in 15–20 minutes. Dry reagent papers retain their sensitivity but moisture is required for the development of color. A 90% acetone-10% water developing solution provides the necessary water but does not dissolve either the sodium bicarbonate support or the AHMT-acetone aminal, provided the contact time is no longer than necessary for moistening.

Calibration curves. Data for two calibration curves were determined: first, with varying exposure times to a fixed formaldehyde concentration of 1.74 ppm; and second, with various concentrations of formaldehyde at a constant exposure time of 300 seconds. The data is summarized below in Tables A and B.

TABLE A
Calibration Data for Reflection Absorbance vs. Time of Exposure to 1.74 ppm Formaldehyde Concentration

| Exposure Time (Seconds) | Reflection Absorbance[1] |
|---|---|
| 50 | 0.051 ± 0.010 |
| 100 | 0.066 ± 0.013 |
| 150 | 0.113 ± 0.009 |
| 200 | 0.140 ± 0.013 |
| 300 | 0.201 ± 0.007 |
| 400 | 0.215 ± 0.012 |
| 500 | 0.237 ± 0.005 |

[1]Mean and standard deviation of 5 determinations at a flow rate of 2000 ml/minute.

TABLE B
Calibration Data for Reflection Absorbance vs. Increasing Concentration of Formaldehyde

| Formaldehyde Concentration (ppm)[1] | Reflection Absorbance[2] |
|---|---|
| 0.24 | 0.064 ± 0.004 |
| 0.49 | 0.087 ± 0.004 |
| 0.71 | 0.101 ± 0.002 |
| 0.97 | 0.110 ± 0.008 |
| 1.22 | 0.121 ± 0.004 |
| 1.48 | 0.129 ± 0.005 |
| 1.74 | 0.136 ± 0.004 |

[1]Constant exposure time of 300 seconds with a flow rate of 2,100 mL/minute.
[2]Mean and standard deviation of 5 or more determinations.

Study of interferences. Qualitative tests were made on several possible interferences by placing the compounds to be tested in 50-ml Ehrlenmeyer flasks and exposing the prepared reagent papers to the vapors for various periods of time.

1. paraformaldehyde (as a standard): exposure time 10 seconds—well-defined purple spot after development.
2. acetaldehyde (pure liquid):
   a. exposure time 20 seconds—negative response.
   b. exposure time 15 minutes—negative response.
3. propionaldehyde (pure liquid): exposure time 20 seconds—negative response.
4. benzaldehyde (pure liquid): exposure time 15 minutes—essentially negative response.

Apparently, only formaldehyde, of the volatile aldehydes, is able to react with the AHMT-acetone aminal to displace acetone. As the —NH—C(CH$_3$)$_2$—NH— bonding is very labile, formaldehyde can displace a volatile ketone such as acetone or methylethyl ketone. On the other hand, a non-volatile ketone such as 4-phenylcyclohexanone does not form a reagent reactive toward formaldehyde because the displaced ketone does not leave the reaction site.

We claim:
1. The process of preparing a colorimetric detector for formaldehyde vapor, comprising:
   (a) coating an inert solid support with a solid phase layer of stable metal bicarbonate;
   (b) applying to said metal bicarbonate layer a solution of 4-amino-3-hydrazino-5-mercapto-1,2,4-triazole (AHMT) in a volatile liquid ketone forming a compound with AHMT from which the ketone can be displaced by formaldehyde; and
   (c) evaporating unreacted ketone from said layer and support to obtain a colorimetric detector sensitive to formaldehyde vapor in the detective range below 2 ppm formaldehyde.
2. The colorimetric detector prepared by the process of claim 1.

3. The process of claim 1 in which said metal bicarbonate is selected from the class consisting of sodium and potassium bicarbonate.

4. The process of claim 1 in which said ketone is selected from the class consisting of acetone and methylethyl ketone.

5. The process of preparing a colorimetric detector for formaldehyde vapor, comprising:
   (a) coating an inert solid support with a solid phase layer of a bicarbonate salt selected from the class consisting of sodium and potassium bicarbonate;
   (b) applying to said metal bicarbonate layer a solution of 4-amino-3-hydrazino-5-mercapto-1,2,4-triazole (AHMT) in a volatile liquid ketone forming a compound with AHMT from which the ketone can be displaced by formaldehyde, said ketone being selected from the class consisting of acetone and methylethyl ketone; and
   (c) evaporating unreacted ketone from said layer and support to obtain a colorimetric detector sensitive to formaldehyde vapor in the detective range below 2 ppm formaldehyde.

6. The colorimetric detector prepared by the process of claim 5.

7. The process of preparing a colorimetric detector for formaldehyde vapor, comprising:
   (a) coating an inert solid support with a solid phase layer of sodium bicarbonate;
   (b) applying to said bicarbonate layer an acetone solution of 4-amino-3-hydrazino-5-mercapto-1,2,4-triazole (AHMT) to form an acetone aminal compound with said AHMT from which acetone can be displaced by formaldehyde; and
   (c) evaporating unreacted acetone from said layer and support to obtain a colorimetric detector sensitive to formaldehyde vapor in the detective range below 2 ppm formaldehyde.

8. The colorimetric detector prepared by the process of claim 7.

* * * * *